(12) United States Patent
Karkanias et al.

(10) Patent No.: US 7,983,933 B2
(45) Date of Patent: Jul. 19, 2011

(54) PATIENT MONITORING VIA IMAGE CAPTURE

(75) Inventors: Chris Demetrios Karkanias, Sammamish, WA (US); Stephen E. Hodges, Cambridge (GB)

(73) Assignee: Microsoft Corporation, Redmond, WA (US)

( * ) Notice: Subject to any disclaimer, the term of this patent is extended or adjusted under 35 U.S.C. 154(b) by 930 days.

(21) Appl. No.: 11/567,455

(22) Filed: Dec. 6, 2006

(65) Prior Publication Data

US 2008/0140444 A1  Jun. 12, 2008

(51) Int. Cl.
*G06Q 10/00* (2006.01)

(52) U.S. Cl. ............. 705/2; 705/3; 705/5; 345/156; 345/619; 700/244; 600/300; 725/105; 382/128

(58) Field of Classification Search .......... 715/700; 713/186; 705/2, 3; 600/407, 137, 300; 340/870.07; 345/619; 700/244

See application file for complete search history.

(56) References Cited

U.S. PATENT DOCUMENTS

| | | | |
|---|---|---|---|
| 6,228,028 B1 * | 5/2001 | Klein et al. ............ 600/437 |
| 7,242,318 B2 * | 7/2007 | Harris ............ 340/870.07 |
| 7,257,832 B2 * | 8/2007 | Beane et al. .......... 725/105 |
| 7,693,729 B2 * | 4/2010 | Yankelevitz et al. ........... 705/2 |
| 7,860,287 B2 * | 12/2010 | Zahlmann et al. ............ 382/128 |
| 2002/0171669 A1 * | 11/2002 | Meron et al. ............ 345/619 |
| 2003/0036683 A1 * | 2/2003 | Kehr et al. ............. 600/300 |
| 2003/0208378 A1 * | 11/2003 | Thangaraj et al. ............. 705/2 |
| 2004/0025030 A1 * | 2/2004 | Corbett-Clark et al. ....... 713/186 |
| 2005/0149869 A1 * | 7/2005 | Kehr et al. ................ 715/700 |
| 2005/0182664 A1 * | 8/2005 | Abraham-Fuchs et al. ...... 705/3 |
| 2005/0251011 A1 * | 11/2005 | Zahlmann et al. ............ 600/407 |
| 2007/0016443 A1 * | 1/2007 | Wachman et al. ............... 705/2 |
| 2007/0206510 A1 * | 9/2007 | Morris et al. ............... 370/252 |
| 2007/0292012 A1 * | 12/2007 | Brandon et al. ............ 382/128 |
| 2008/0052112 A1 * | 2/2008 | Zahlmann et al. ............... 705/2 |
| 2008/0119958 A1 * | 5/2008 | Bear et al. ..................... 700/244 |

FOREIGN PATENT DOCUMENTS

| | | |
|---|---|---|
| KR | 10-2000-0076025 A | 12/2000 |
| KR | 10-2001-0050099 A | 6/2001 |
| KR | 10-2004-0012155 A | 2/2004 |
| KR | 10-2006-0032243 A | 4/2006 |
| KR | 10-2006-0064885 A | 6/2006 |

OTHER PUBLICATIONS

Penn medicine to use Informedix's Med-eMonitor System in stroke prevention pilot program; Business wire press release; Aug. 22, 2006.*
Google search results.*
Dialog search results.*
International Search Report and Written Opinion dated May 19, 2008 for PCT Application U.S. Appl. No. PCT/US2007/086596, 10 Pages.
Israel Office Action dated Apr. 22, 2010 for Israel Patent Application U.S. Appl. No. 198056, 2 pages.

* cited by examiner

*Primary Examiner* — Dilek B Cobanoglu
(74) *Attorney, Agent, or Firm* — Turocy & Watson, LLP

(57) ABSTRACT

A system that can enable clinical trial compliance determination by viewing sequences of images captured during an event is disclosed. For example, the innovation can employ captured event sequences to enable a subject or third party to assess a subject's actions related to a medical trial. The capture of event sequences can be triggered based upon sensory data, radio frequency identification (RFID) data, pattern recognition data, etc. The system also provides mechanisms to locate images or sequences, playback images or sequences or images as well as to set compliance parameters associated with a particular clinical trial.

17 Claims, 15 Drawing Sheets

PATIENT MONITORING VIA IMAGE CAPTURE

BACKGROUND

A clinical trial commonly refers to a rigorously controlled test of a new drug or a new invasive medical device on human subjects or patients. Prior to being made available to general population for use, in the United States, drugs and invasive medical devices must pass this rigorous testing set forth commonly known as a clinical trial. Compliance of clinical trials is regulated by the Food and Drug Administration (FDA) which is a federal agency responsible for overseeing trade in and the safety of food and drugs in the United States.

Today, the most commonly performed clinical trials are used to evaluate drugs or medical therapies in strictly scientifically controlled settings. Probably the most important purpose of such trials is to determine whether the drugs or treatment options are safe, effective, and better than the current standard of care presently available. Because the potential effects of incorrectly assessing a drug or medical therapy can be catastrophic, extreme care must be given in monitoring patient's health and progress.

Conventionally, most clinical trials, especially drug trials, are designed to be randomized and oftentimes include placebo substitutes for the actual drug on trial. Essentially, each subject is randomly assigned to receive a medication or treatment, which might in fact be the placebo rather than the actual drug on trial. In may cases, neither the subjects nor individuals monitoring the study know which treatment is being administered to any given subject; and, in particular, none of those involved in the study know which subjects are being administered a placebo.

Throughout the trial, subjects are monitored both within a controlled setting as well as throughout daily life. As such, oftentimes, a written journal or record is kept that memorializes events such as, when the drug was taken, what dosage was taken, what effects, if any, were felt after taking the medication, etc. This manually gathered data is analyzed and recorded in order to determine compliance within the scope of the FDA regulated clinical trial. However, the self-reporting mechanisms (e.g., written journals and records) are notorious causes of inaccurate data. Moreover, manual supervision and reporting is burdensome and extremely costly to the patient as well as to the clinical trial as a whole.

Today, many clinical trials require large numbers of participants in order to obtain useful results as well as to adhere to FDA guidelines. Oftentimes, trials take place in multiple geographical areas or even countries. As the subjects of the trials become more and more dispersed, monitoring and regulating dosage, effects, etc. is becoming increasingly difficult and expensive. Moreover, the size of the class of participants as well as the distributed nature of the participants can also lead to an increase the margin of error and thus, an increase in risk of to the public in the event of an incorrectly justified FDA approval.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises a system that can facilitate automatic compliance determinations related to clinical trials. By way of example, the system can be used to capture visual images related to a subject's use of a medicine, treatment, medical device, etc. These images can later be reviewed and compared to compliance criteria of the medical or clinical trial. As well, the system described herein can be employed to visually monitor most any action taken by a patient or individual. In any case, these images can be analyzed via a compliance tracker component to render a compliance result. In aspects, this analysis can be automatic or manual as desired.

An event recorder component can be used to capture the images associated with events during a clinical trial. Image capture can be prompted or triggered in a variety of ways including, but not limited to, based upon sensor data (e.g., environmental, physiological), radio frequency identification (RFID) tags, pattern recognition (e.g., via a scanner), etc. Moreover, information gathered by these triggering techniques can also be used to annotate the captured images. These annotations can later be used to assist in establishing compliance associated with clinical trial criteria.

In addition to determining compliance, aspects of the innovation can manage and/or promote compliance by alerting a subject of a deviation of a compliance parameter. For instance, an alert can be generated and sent to remind a subject to take a dose of a medication, perform additional repetitions of therapy, eat food with a dose of medication, etc. These alerts can be audible, visual, vibratory, etc.

Other aspects disclose an interface component that enables interaction to view captured images as well as to manage trial parameters. For instance, an image playback component can be provided that enables display of captured images. This visual display can assist in compliance determination. A criteria management component can be provided that enables compliance parameters to be programmed or modified as desired. As well, a sequence retrieval component can be provided that enables a user, or third party, to rapidly locate a desired sequence or image within a sequence. For example, annotations or tags can be used to locate desired images or points in time within an event or clinical trial.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
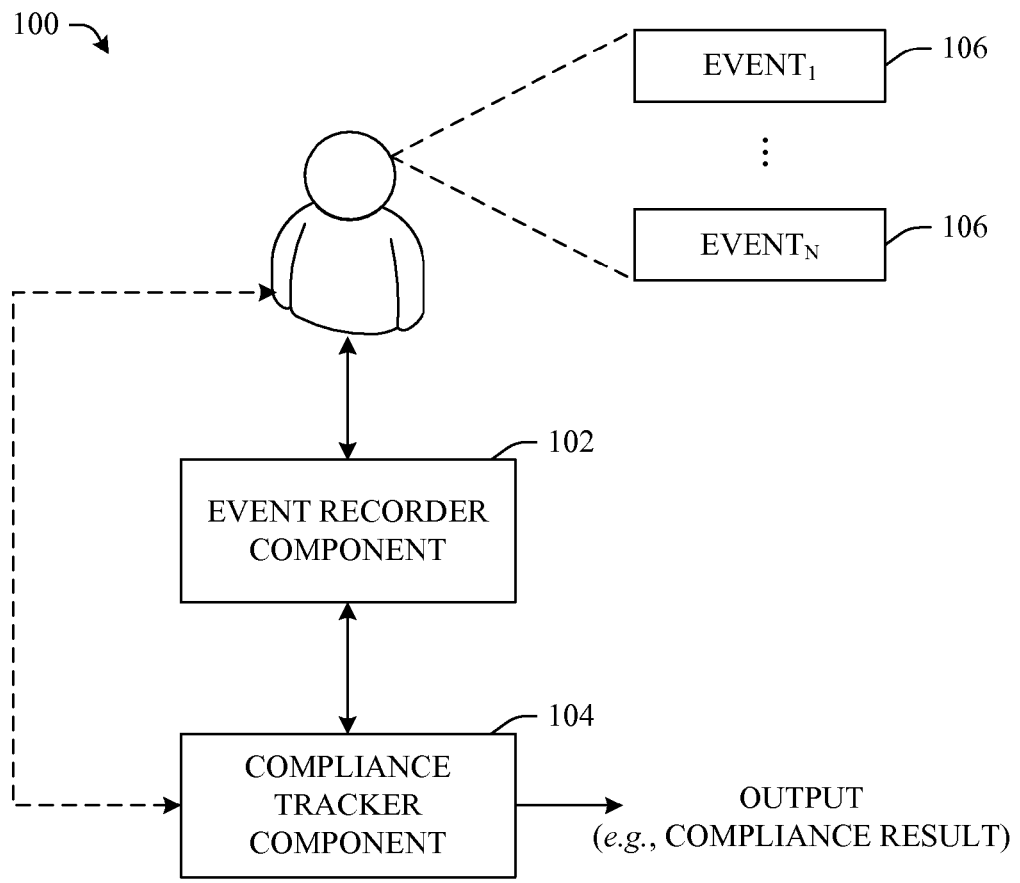
FIG. 1 illustrates an example system that facilitates employing event image sequences in clinical trial compliance determinations.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

The subject innovation is directed to systems and methods that can assist in assessment of actions and/or events associated with the testing of medications and other treatments as well as most any other action taken by a patient or individual. In particular aspects, the innovation can be employed to assist in regulated (or non-regulated) clinical trials associated with drugs and other medications prior to availability to the public for general use. While a large part of a clinical trial is manual recordation of dosage information, timing, effect, etc., the innovation can be used to automatically capture images associated with the phases of the clinical trial. These images can be used in compliance assessment of the subject as a function of the clinical trial. For example, the innovation can capture images and other information (e.g., physiological data) associated with a subject (e.g., patient) which can be used in view of the clinical trial.

Still further, although most of the aspects described herein are directed to clinical trials, it is to be appreciated that the innovation can be employed to monitor most any action taken by a patient or individual. For example, the systems described herein can be employed in weight loss programs where it may be desirable to monitor a particular amount or type of food intake. Similarly, exercise patterns can be monitored to ensure compliance with a prescribed routine. With regard to clinical trials, the systems can also be employed to monitor ingestion of the correct drugs, correct dosage of those drugs as well as adherence to instructions (e.g., take with food) so as to not compromise the efficacy of the treatment, for example, by eating incorrect foods or engaging in appropriate activities during the clinical trial.

Essentially, the innovation discloses systems and/or methods that can employ the captured information to establish compliance as a function of some predetermined criteria. As well, systems and methods can automatically regulate compliance, for example, by delivering notifications in the event of a compliance deviation. In doing so, captured information can be analyzed to determine if a subject is adhering to criteria associated with a clinical trial and, if not, suggestions (via notifications) can be made to prompt adherence.

Referring initially to the drawings, FIG. 1 illustrates a system 100 that employs captured images to manage and/or monitor compliance in accordance with a clinical trial. As illustrated, generally, the system 100 includes an event recorder component 102 and a compliance tracker component 104 that together manage and/or monitor clinical trial compliance. In operation, the event recorder component 102 can automatically record images of related to 1 to N events related to a trial within a given period of time. It is to be understood that 1 to N events can be referred to individually or collectively as events 106.

In more particular aspects, the event recorder component 102 can be employed to capture images related to actions of a user related to a clinical trial. The granularity and frequency of the captured events can be programmed, pre-programmed or contextually triggered via the event recorder component 102. By way of example, the event recorder component 102 can be equipped with sensors (e.g., light sensors, location sensors, motion sensors) whereby when a change in a designated criterion is detected, an image of the event 106 is captured.

The compliance tracker component 104 can be employed to automatically monitor captured images in order to determine compliance of a clinical trial. For example, the images can be analyzed to verify dosage of a medication, timing of a medication and associated effect upon a subject when the medication was used. Additionally, physiological and/or environmental data associated with the subject can be captured and subsequently used to tag or annotate an image sequence. This physiological and/or environmental data can assist in establishing compliance with predetermined trial criteria.

It is to be understood and appreciated that the event recorder component 102 can be a wearable image capture device (e.g., camera) that establishes a digital record of the events 106 that a person experiences. The nature of the device (102) is to capture these recordings automatically, without any user intervention and therefore without any conscious effort. However, image capture can also be user-initiated in other aspects.

As described supra, one rationale of the event recorder component 102 is that a captured digital record of an event 106 can subsequently be reviewed in order to determine compliance of and to assist with clinical trial(s) (e.g., via compliance tracker component 104). As well, review of the captured images can be used to assist in prompting, notifying or alerting a subject of a deviation of a trial parameter.

Figure 2:
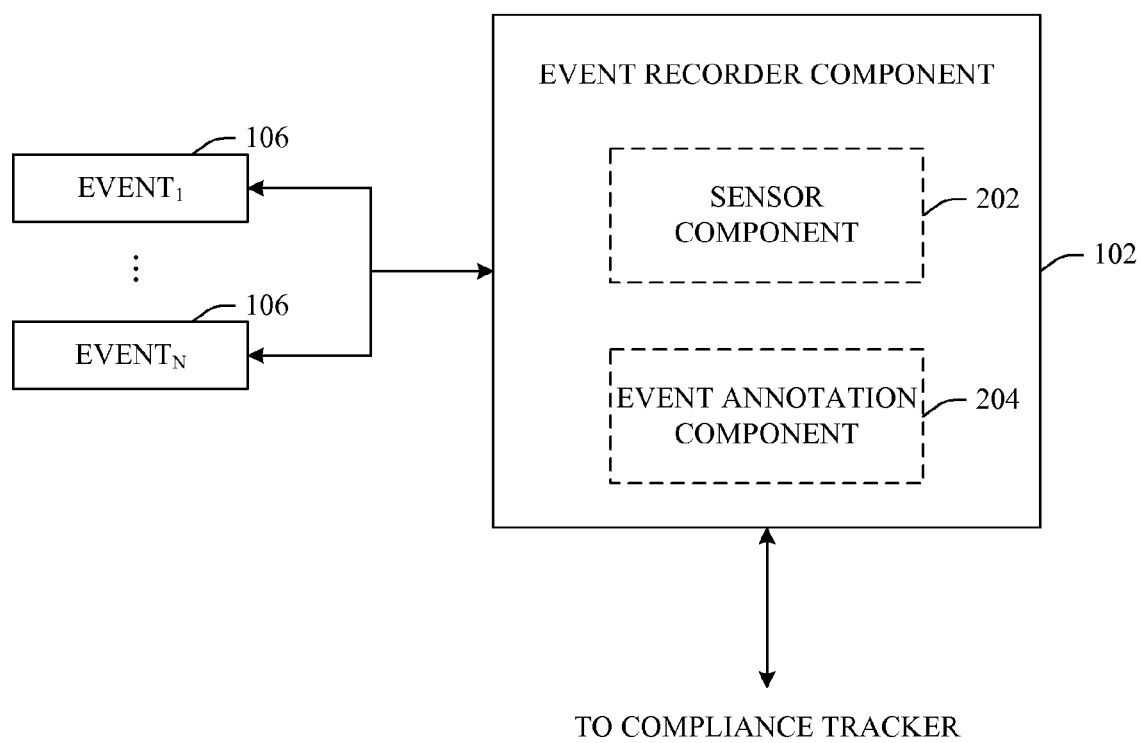
FIG. 2 illustrates a block diagram of an example event recorder component having a sensor component and an event annotation component in accordance with an aspect of the innovation.

Turning now to FIG. 2, a block diagram of an event recorder component 102 is shown. As illustrated, the event recorder component 102 can include a sensor component 202 and an optional event annotation component 204 which facilitate prompting action and index with regard to the images. Essentially, the sensor component 202 can be used to trigger the capture of an image from the event recorder component 102.

The optional event annotation component 204 can facilitate annotating (or tagging) image sequences. As described above, sensor data can be captured and used to annotate an image sequence. In addition to enhancing playback, this annotation can be used to recreate events related to the monitored clinical trial.

Figure 3:
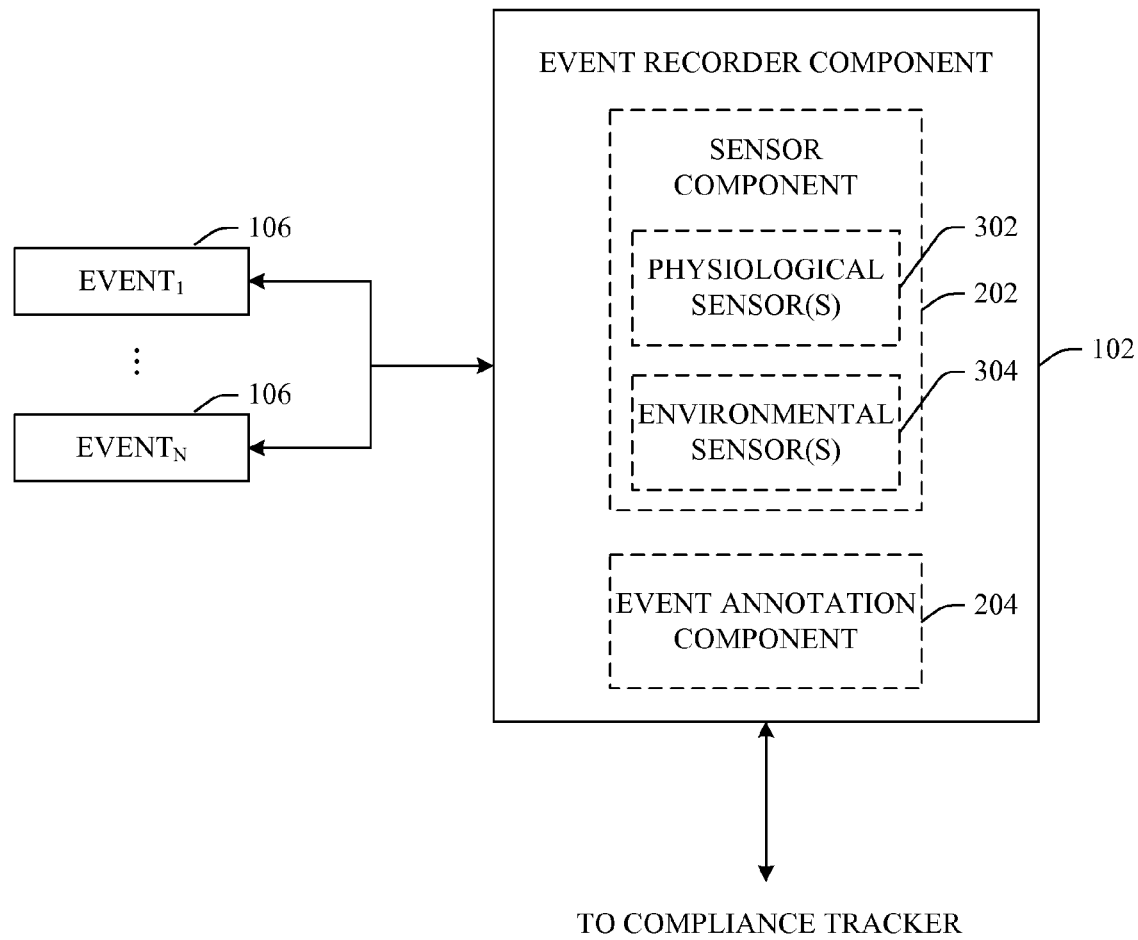
FIG. 3 illustrates a block diagram of an event recorder having a physiological sensor component and an environmental sensor component in accordance with an aspect of the innovation.

Referring now to FIG. 3, the sensor component 202 can include either or both physiological and/or environmental sensors (302, 304). In operation, these sensors can be used to trigger image capture as well as to gather information and data to be used in annotating images. For instance, when a specific threshold is reached, an image or series of images can be automatically captured and annotated with the data related to the triggering threshold. Similarly, when an image is captured, environmental and/or physiological data can be simultaneously captured and employed to annotate captured images.

By way of example, the event recorder component 102 can automatically capture an image of an event 106 associated with a clinical trial, for example, an image of a subject taking a dosage of a medication. In addition to capturing the image of the event 106, the event recorder component 102 (via sensors 302, 304) can monitor physiological criterion such as heart rate, blood pressure, body temperature, blood sugar, blood/alcohol concentration, etc. associated with the event 106. As well, environmental data such as location, ambient temperature, weather conditions, etc. can be captured. Thus, this annotated data related to the event 106 can be used to more intelligently assess the compliance with a given clinical trial.

At a low level, the system 100 can be employed to capture image sequences related to events 106 (e.g., times associated with ingestion of a medication, amount of dosage). This information can be used to ensure compliance, for example timing, dosage, etc. Additionally, environmental data (e.g., ambient temperature, location, motion) can be captured to assist in analysis of events 106 related to a clinical trial. Moreover, physiological data can be captured and employed to further assist in analysis of events 106 associated with a clinical trial.

In other aspects, the system 100 (and more particularly, the event recorder component 102) can effectively be employed as an information hub for a patient in a clinical trial. For example, it is to be appreciated that a series of specialized sensors that integrate with the event recorder component 102, for example, via some wireless link (e.g., Bluetooth, infrared, IEEE 802.11, cell network) can be employed. In this way, event recorder components 102 could have a general core of data collection (e.g., global position system data (GPS), image data, temperature data, audio data, motion data, identification gathered data) but could be adapted to specific experimental measures with what, in effect, could be modular 'add-ons.' By way of further example, vital sign sensors, a pulse-oximeter, a stretch or range-of-motion sensor, skin galvanic response measuring sensor, or a gait sensor (pressure sensitive insert in your shoes) could be employed as modular 'add-ons' to the core event recorder component 102. Thus, the event recorder component 102 can be employed as an overall information hub for information and data related to the clinical trial.

Figure 4:
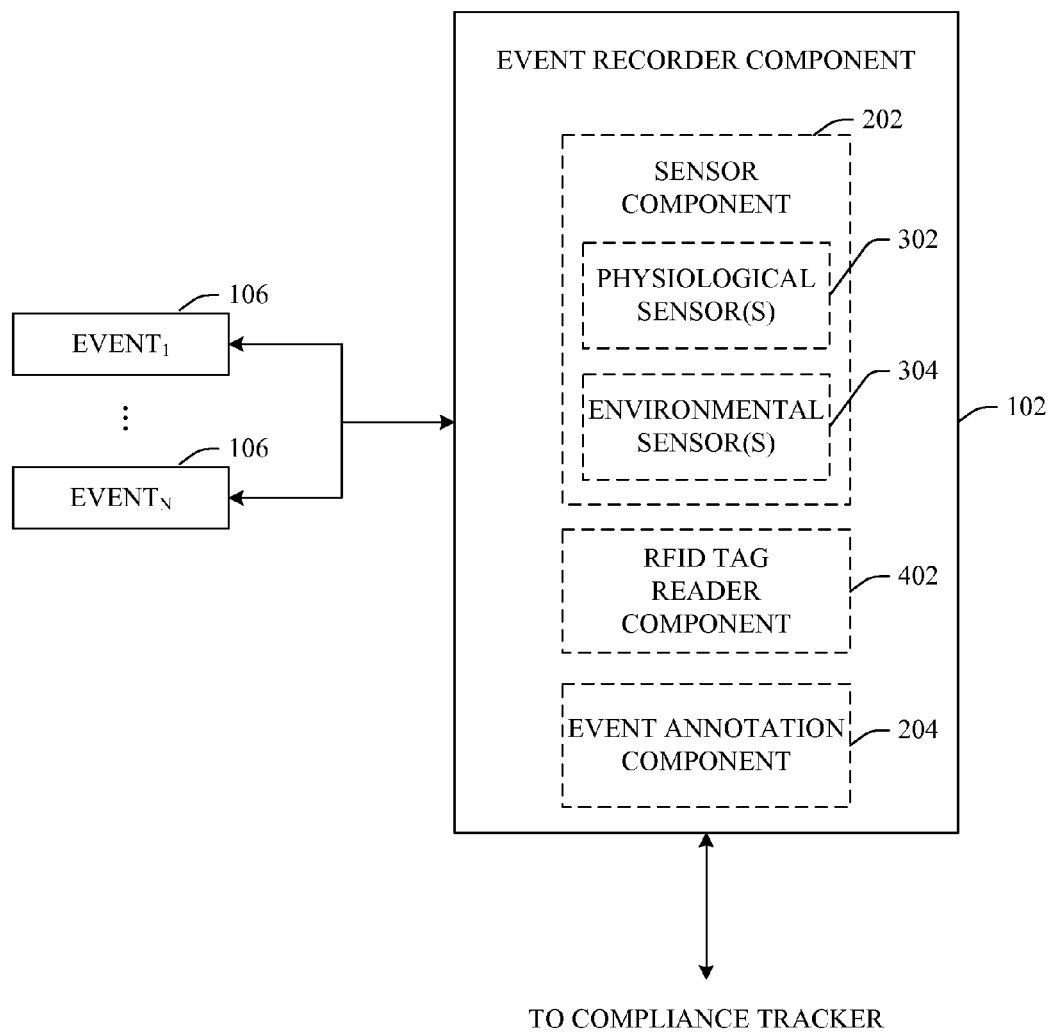
FIG. 4 illustrates an example event recorder component having a radio frequency identification (RFID) tag reader component in accordance with an aspect of the innovation.

Referring now to FIG. 4, an alternative block diagram of event recorder component 102 is shown to include a radio frequency identification (RFID) tag reader component 402. This RFID tag reader component 402 component can be used to identify RFID equipped devices, products, locations, etc. In one particular aspect, a medication container or packaging (e.g., bottle) can include an RFID transponder whereby the RFID tag reader component 402 can receive this information and make appropriate determinations thereafter. More particularly, a medication pill bottle can include an RFID transponder thus, when the event recorder component 102 captures an image of a subject ingesting a dosage of a medication, the RFID information can be used to identify the exact medication, dosage, etc. taken.

As described above, this information can be used by the event annotation component 204 to annotate or tag the captured image or sequence. It will be appreciated that this annotation can be particularly useful in situations where multiple medication containers (e.g., bottles) appear within the captured image. Moreover, as will be described below, this identification information (e.g., RFID tag information) can also be used to prompt compliance with a clinical trial as well as to assist in avoidance of mistakes with respect to medication type, dosage, timing, etc.

Although the aforementioned example is directed to RFID transmission/reception of information, it is to be understood that most any wireless transmission techniques (e.g., Bluetooth) can be used without departing from the spirit and scope of the innovation. As well, in addition to or in lieu of a wireless transmission protocol, other identification techniques can be used to ensure correct identification of medications being used. For example, pattern recognition techniques can be used to determine label designs, colors, etc. in order to enable medication identification. In other aspects, speech recognition mechanisms can be enabled to automatically a voice command from a subject thereafter converting the speech to metadata which can be annotated to an appropriate image or sequence of images.

Figure 5:
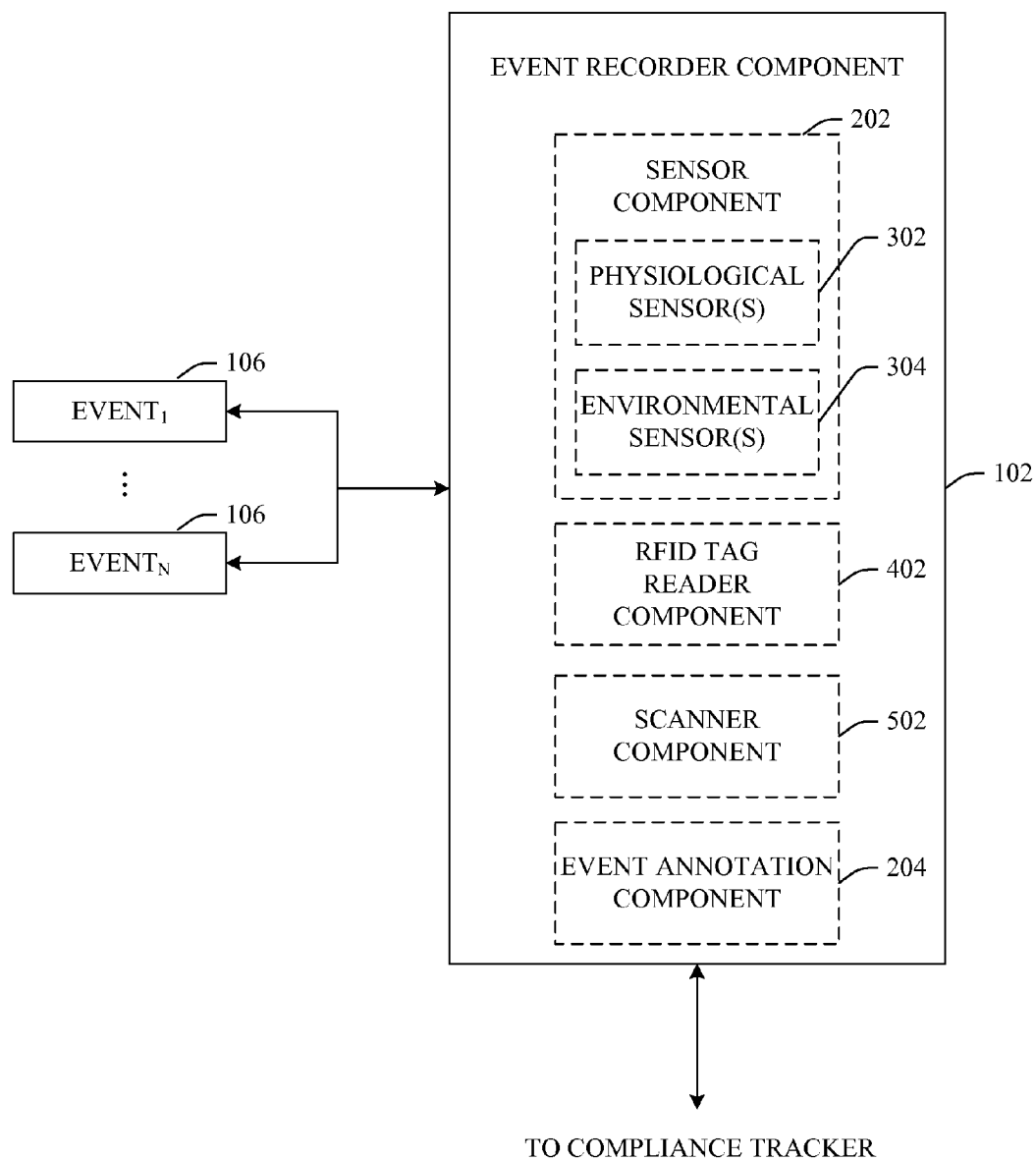
FIG. 5 illustrates an example event recorder component having a scanner component in accordance with an aspect of the innovation.

FIG. 5 illustrates still another example of an event recorder component 102 where a scanner component 502 can be used in medication identification. For instance, as described above, the scanner component 502 can employ pattern recognition to facilitate identification of medications. In another aspect, the scanner component 502 can be employed to detect and decipher a barcode or other identifying symbol located upon a medication container (e.g., bottle label).

In the example of barcode or other identifying symbol, it will be understood that other information can be encoded into the barcode and/or symbol. For instance, information that identifies the subject, type of medication, dosage amount, dosage interval, etc. can be encoded within the barcode or symbol. As will be appreciated, this information can be employed by the event annotation component 204 to tag images associated to a particular medication or drug. In this manner, the subject innovation can be used to monitor trials associated one or more medications.

Figure 6:
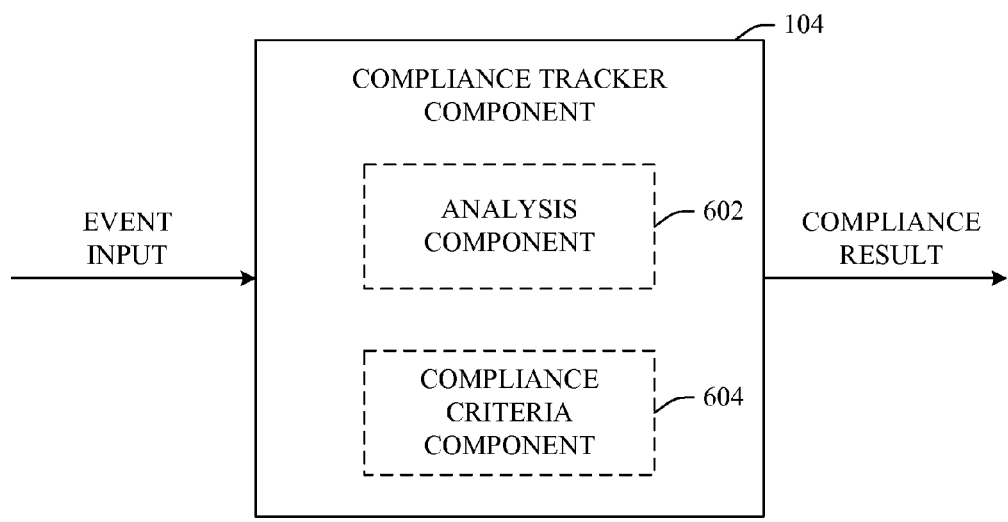
FIG. 6 illustrates an example compliance tracker component that employs an analysis component and a compliance criteria component in accordance with an aspect of the innovation.

Referring now to FIG. 6, a block diagram of compliance tracker component 104 is shown. As illustrated, the compliance tracker component 104 can include an analysis component 602 and a compliance criteria component 604. Each of these components (602, 604) facilitate automatic compliance determination. In other words, while in a simple scenario, images and image sequences can be viewed in order to manually determine compliance with a clinical trial, the analysis component 602 together with the compliance criteria component 604 can facilitate automatic compliance determination.

Figure 7:
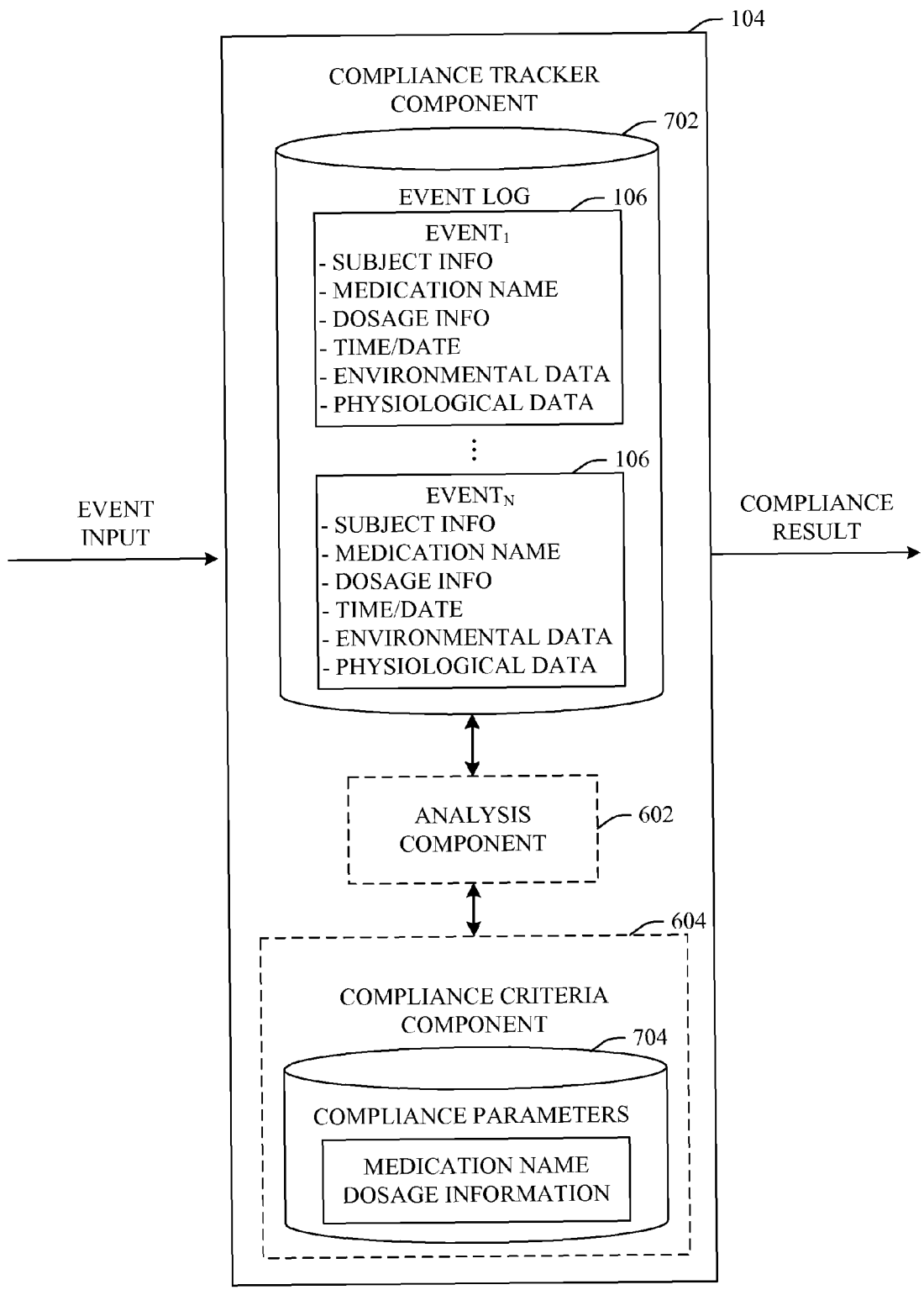
FIG. 7 illustrates an architecture of a compliance tracker component that illustrates example data that can be maintained and compared with respect to an event in order to determine compliance of a clinical trial.

FIG. 7 illustrates a more detailed block diagram of compliance tracker component 104. Essentially, FIG. 7 illustrates that compliance tracker component 104 can include an event log 702 and a compliance parameter store 704. Although the event log 702 and the compliance parameter store 704 are shown as being co-located integral to the compliance tracker component 702, it is to be understood that these both or either of these components can be remotely located without departing from the spirit and scope of this disclosure and claims appended hereto.

As shown, the event log 702 can be employed to store information associated to each of the captured events 106. In addition to captured image data, other data can be stored associated with each of the events 106. For example, information related to the subject, medication name, dosage information, time/date, environmental data, physiological data, etc. can be maintained in connection with each of the recorded events 106.

The analysis component 602 can employ the event log 702 to automatically establish a compliance result as shown. In operation, the analysis component 602 can compare the captured information maintained within the event log 702 to compliance parameters 704. The compliance parameters 704 can include specific, and acceptable (e.g., thresholds) parameters and limits related to a particular clinical trial. In a simple example, the compliance parameters 704 can include medication names and related dosage information. Other information can include timing, prerequisites to taking (e.g., take with food), etc. The criteria can be used by the analysis component 602 to determine compliance or non-compliance as appropriate.

Figure 8:
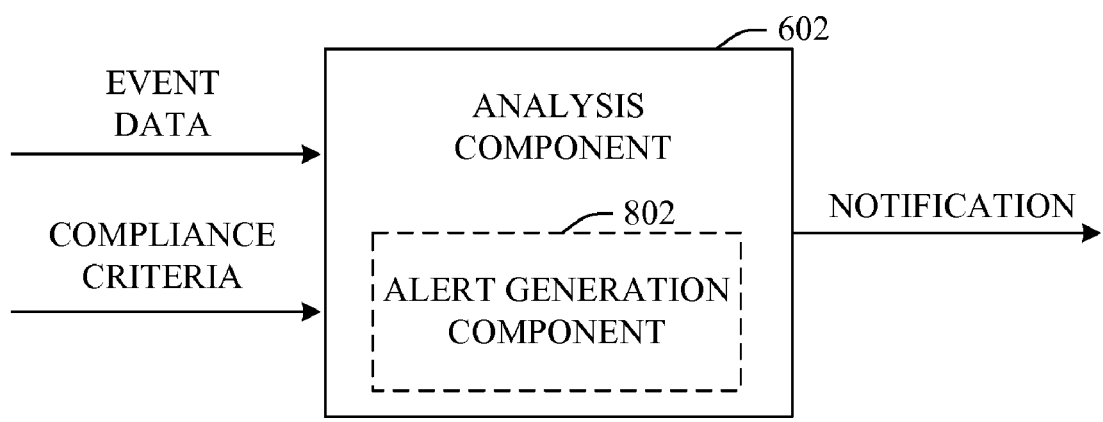
FIG. 8 illustrates a block diagram of an analysis component having an alert generation component in accordance with an aspect of the innovation.

In addition to determining overall compliance, the analysis component 602 can be used to prompt deviation or compliance information. As shown in FIG. 8, the analysis component 602 can include an alert generation component 802 that establishes an alert/notification of a non-compliance and/or deviation of compliance. This alert/notification can be established as a function of the event 106 in view of the compliance parameters 704. It is to be understood that the notification can be of most any form including, but not limited to, audible, visual, text, vibratory, etc.

Figure 9:
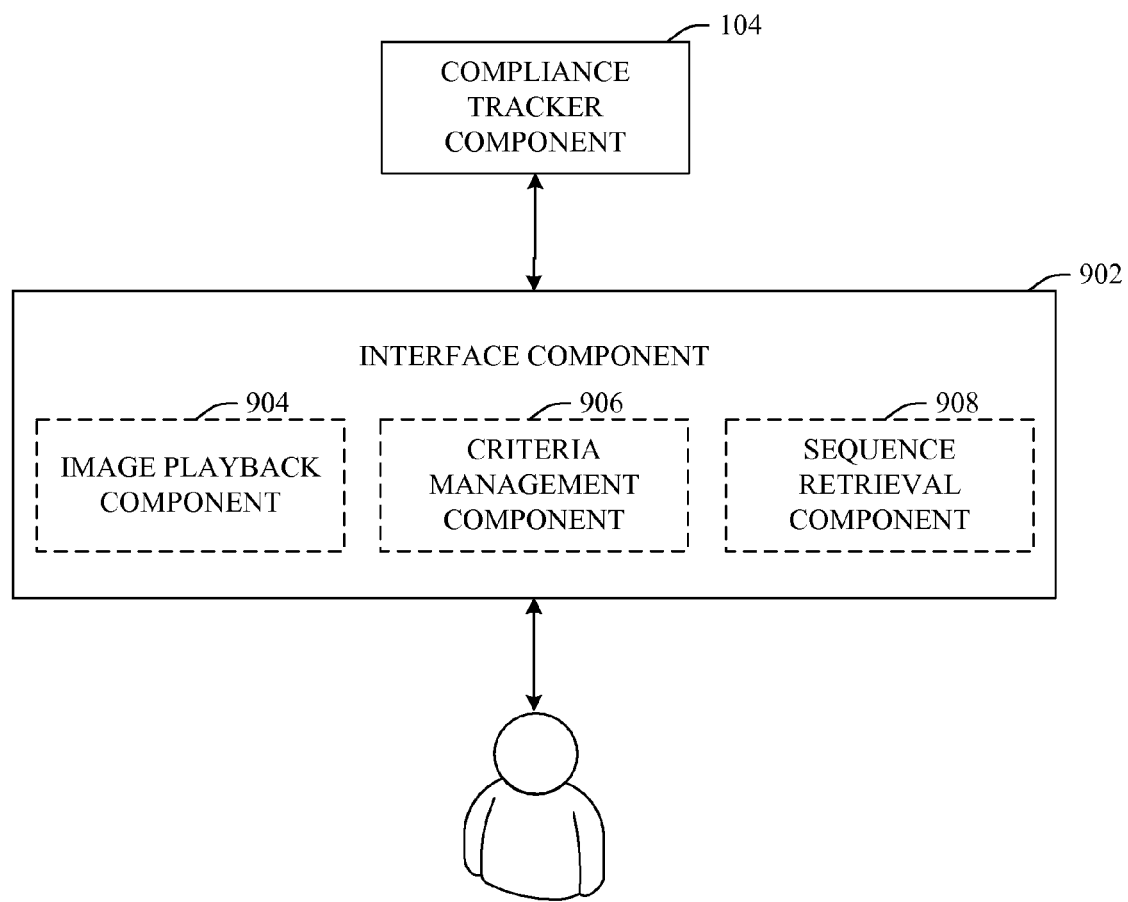
FIG. 9 illustrates a block diagram of an example interface component having an image playback component, a criteria management component and a sequence retrieval component in accordance with an aspect of the innovation.

FIG. 9 illustrates an interface component 902 that enables a user to interact with the compliance tracker component 104. More particularly, interface component 902 can include an image playback component 904, a criteria management component 906 and a sequence retrieval component 908. Although each of these components are shown inclusive of the interface component 902, it is to be understood that each of the components (904, 906, 908) can be employed independent of the others without departing from the spirit and/or scope of this disclosure and claims appended hereto.

In operation, the image playback component 904 can be employed to visually review images of events 106 captured via the event recorder component (102 of FIG. 1). The criteria management component 906 can enable setting compliance criteria in accordance with a clinical trial. Finally, the sequence retrieval component 908 provides a mechanism whereby a user (or third party) can search for and retrieve images related to a clinical trial. Essentially, the interface component 902 provides mechanisms whereby a user (or third party) can interact with the compliance tracker component 104. These components (904, 906, 908) enable a user to program specific settings related to a trial as well as to effectuate analysis of captured images in view of a clinical trial.

It is to be understood and appreciated that the interface component 902 could also be equipped with a sensor data playback/visualization component (not shown). For instance, this component can enable a monitoring entity (e.g., health care professional) to access and playback information captured via the sensory technologies described supra. These additional aspects are to be considered a part of the disclosure and claims appended hereto.

Figure 10:
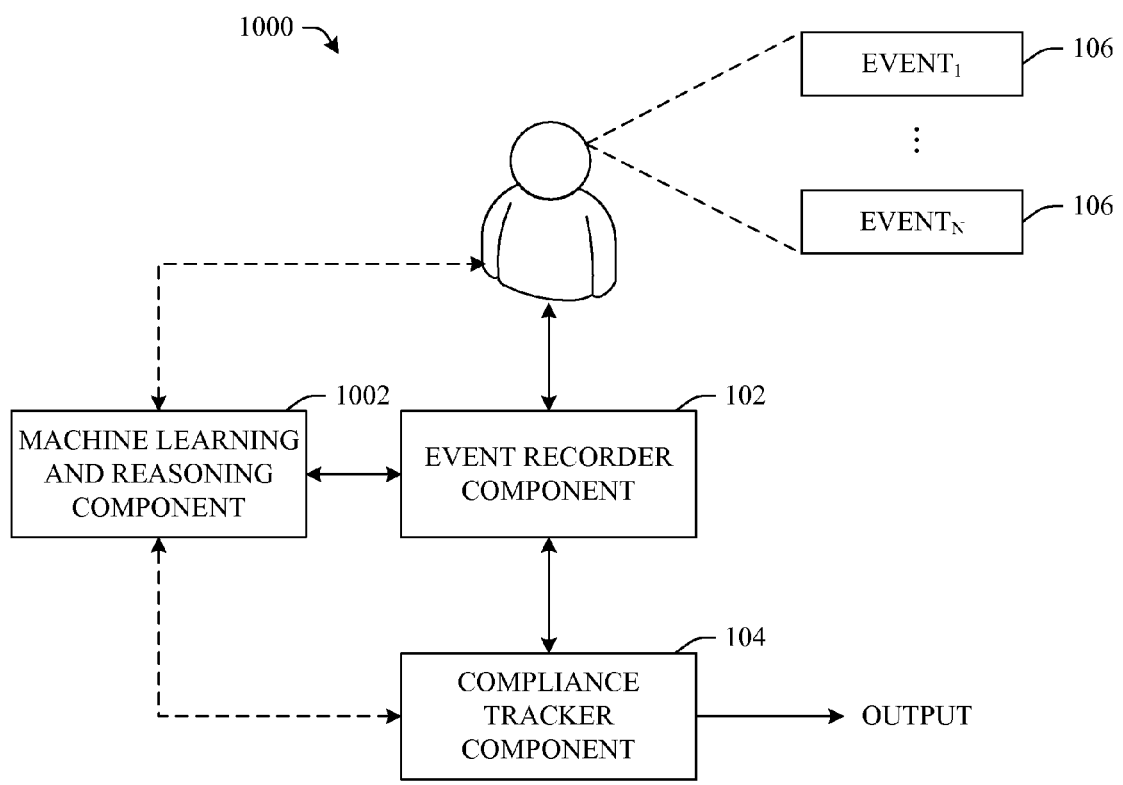
FIG. 10 illustrates an architecture including a machine learning and reasoning component that can automate functionality in accordance with an aspect of the innovation.

FIG. 10 illustrates a system 1000 that employs machine learning and reasoning (MLR) component 1002 which facilitates automating one or more features in accordance with the subject innovation. The subject innovation (e.g., in connection with prompting image capture, establishing compliance, notification) can employ various MLR-based schemes for carrying out various aspects thereof. For example, a process for determining when to trigger the event recorder component 102 to begin capture can be facilitated via an automatic classifier system and process. Moreover, MLR techniques can be employed to automatically establish compliance criteria, assess compliance, etc.

A classifier is a function that maps an input attribute vector, $x=(x1, x2, x3, x4, xn)$, to a confidence that the input belongs to a class, that is, $f(x)=confidence(class)$. Such classification can employ a probabilistic and/or statistical-based analysis (e.g., factoring into the analysis utilities and costs) to prognose or infer an action that a user desires to be automatically performed.

A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated from the subject specification, the subject innovation can employ classifiers that are explicitly trained (e.g., via a generic training data) as well as implicitly trained (e.g., via observing user behavior, receiving extrinsic information). For example, SVM's are configured via a learning or training phase within a classifier constructor and feature selection module. Thus, the classifier(s) can be used to automatically learn and perform a number of functions, including but not limited to determining according to a predetermined criteria when to trigger capture of an image, how/if to annotate an image, what thresholds should be set for compliance, what granularity to capture images (e.g., number of frames per second), etc.

Figure 11:
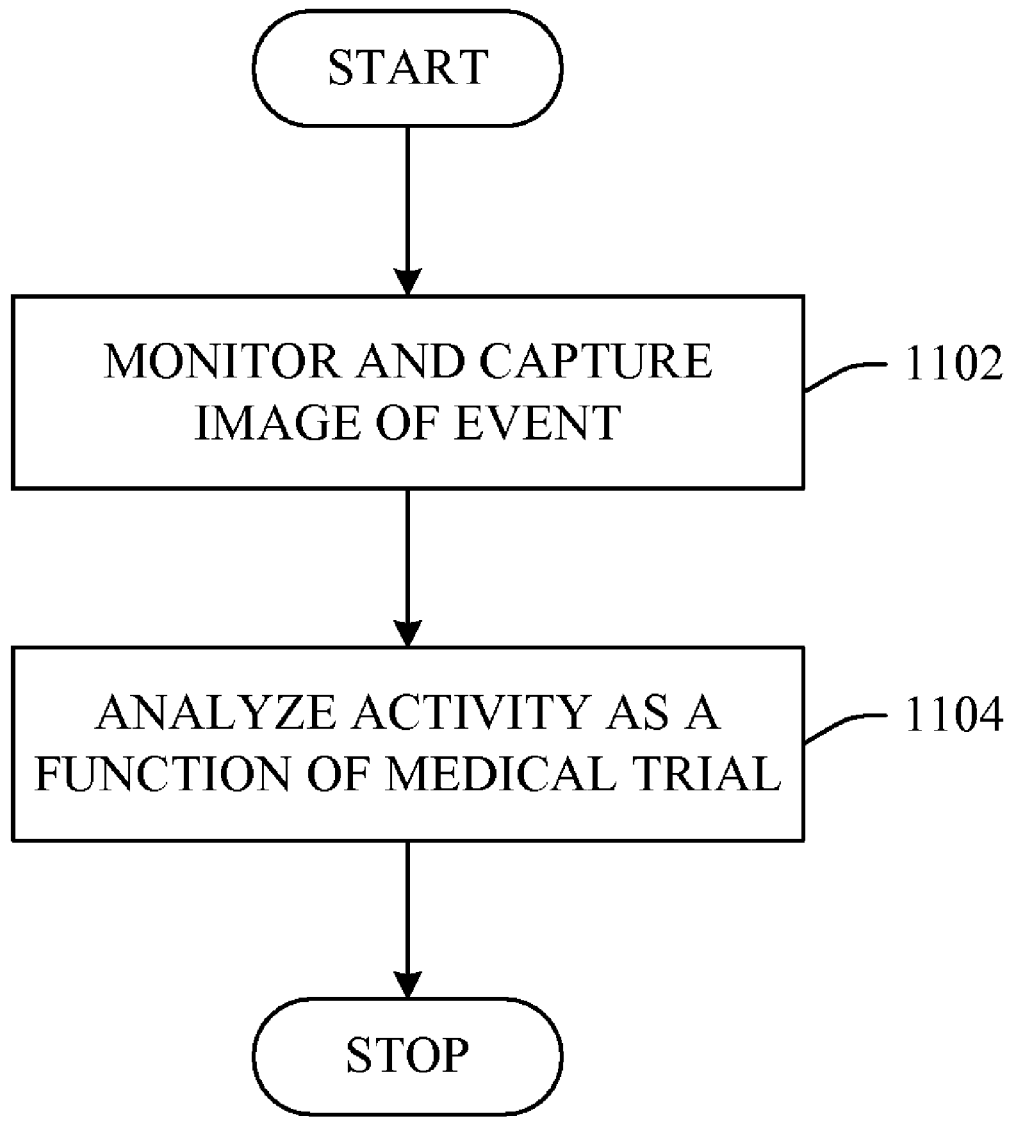
FIG. 11 illustrates an exemplary flow chart of procedures that facilitate compliance determination via viewing image sequences of event activity in accordance with an aspect of the innovation.

FIG. 11 illustrates a methodology of employing a sequence of event images in a medical trial in accordance with an aspect of the innovation. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

At 1102, events can be monitored. In examples, an event can be a specified period of time or an interval within a period of time. Still further, an event can be defined by a specific action of a user or subject. For instance, an event can be administering a dose of a drug or other medication.

Continuing at 1102, image sequences of events are captured. As described above, the granularity of the capture of images can be based upon the nature of the clinical trial or dosage criteria related to a medication or treatment. Thus, the granularity can be preprogrammed or inferred based upon regulations imposed upon a medical trial. It will be understood that the image capture can be triggered based upon environmental sensors, physiological sensors, RFID technology, scanning technology, time-based mechanisms or the like.

At 1104, the captured images can be employed to analyze activity as a function of the medical trial. In other words, a user, auditor or other third party can view the images in order to determine compliance with a clinical trial. For instance, the images can be used to determine if medicine was taken at the correct interval(s), if the correct dosage was taken, etc. It is to be understood that the analysis can occur after all events are monitored or could possibly occur in real-time. For example, intelligence could be employed to automatically perform analysis during (as well as immediately following) an event. Similarly, a link (e.g., wireless link) could be employed to upload images to enable remote analysis either automatically and/or manually as desired.

Figure 12:
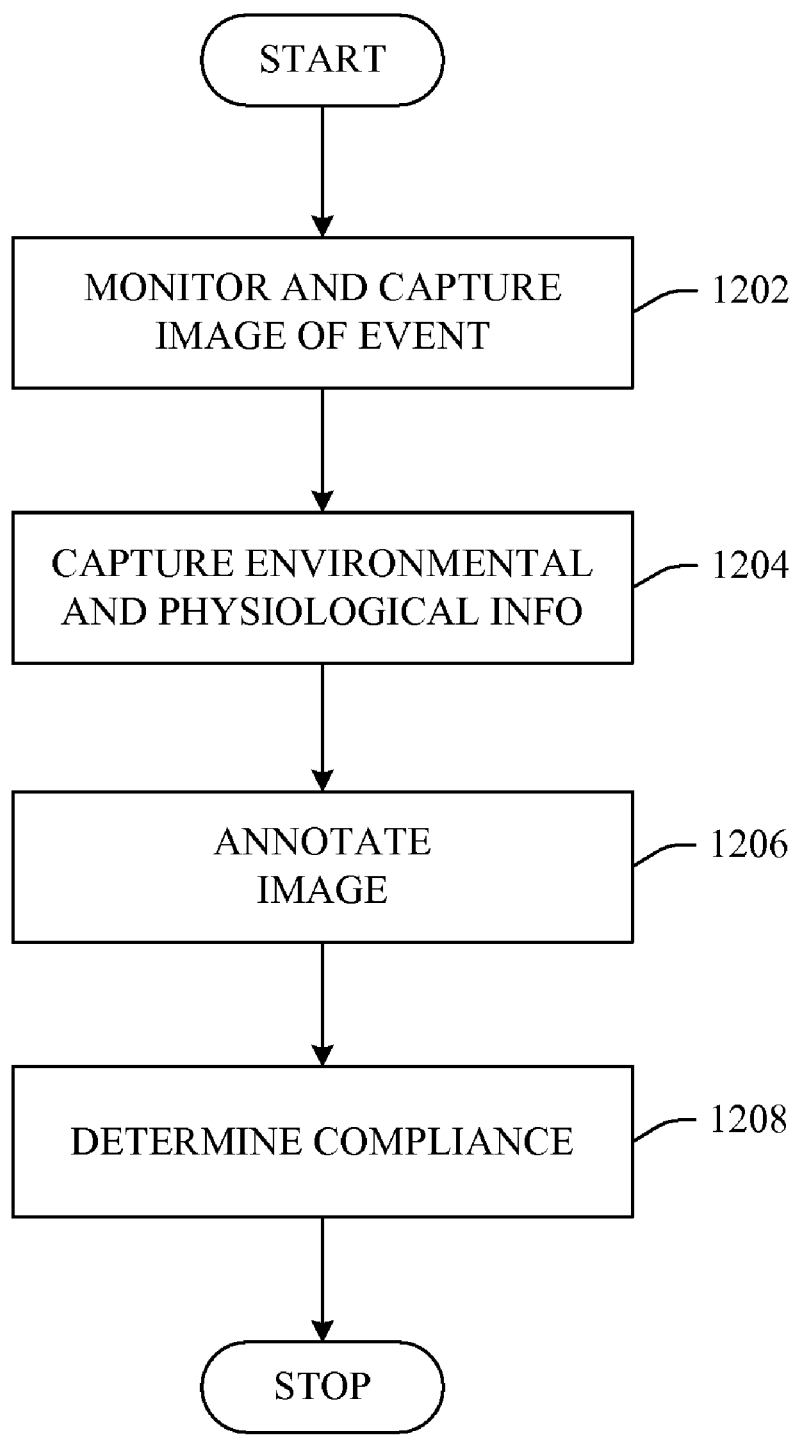
FIG. 12 illustrates an exemplary flow chart of procedures that facilitate annotating image sequences with context data (e.g., physiological, environmental) in accordance with an aspect of the innovation.

Referring now to FIG. 12, there is illustrated a methodology of determining compliance with a medical trial by annotating images in accordance with the innovation. Specifically, at 1202, user activity related to a clinical trial can be monitored. For instance, the system can monitor actions as they relate to a medical prescription.

Images related to an event (or sequence of events) can also be captured at 1202. The capture of these images can be triggered as a function of the sensor data, RFID data, preprogrammed interval data, etc. For example, a proximity sensor can be employed to trigger image capture when a subject is within a certain distance of an RFID equipped medicine container.

Additionally, as described supra, at 1204, external data related to an event can be captured via physiological and/or environmental sensors. As well, RFID and scanner technology can be employed to supplement the activity information.

Once captured, the images and/or sequences of images can be annotated with contextual data (and other sensor-provided data) at 1206. These annotations can provide additional data to assist in determination and effects within the scope of a clinical trial. At 1208, the annotated images can be employed to determine compliance with the parameters of a medical trial.

Although both FIG. 11 and FIG. 12 are illustrated in the form of a linear flow diagram, it is to be understood that the acts described can be performed recursively in accordance with additional events or portions thereof. As well, it is to be understood that analysis and/or compliance determination need not occur after all images are captured. Rather, analysis and/or compliance can be determined at any time (e.g., in real-time) as desired.

Figure 13:
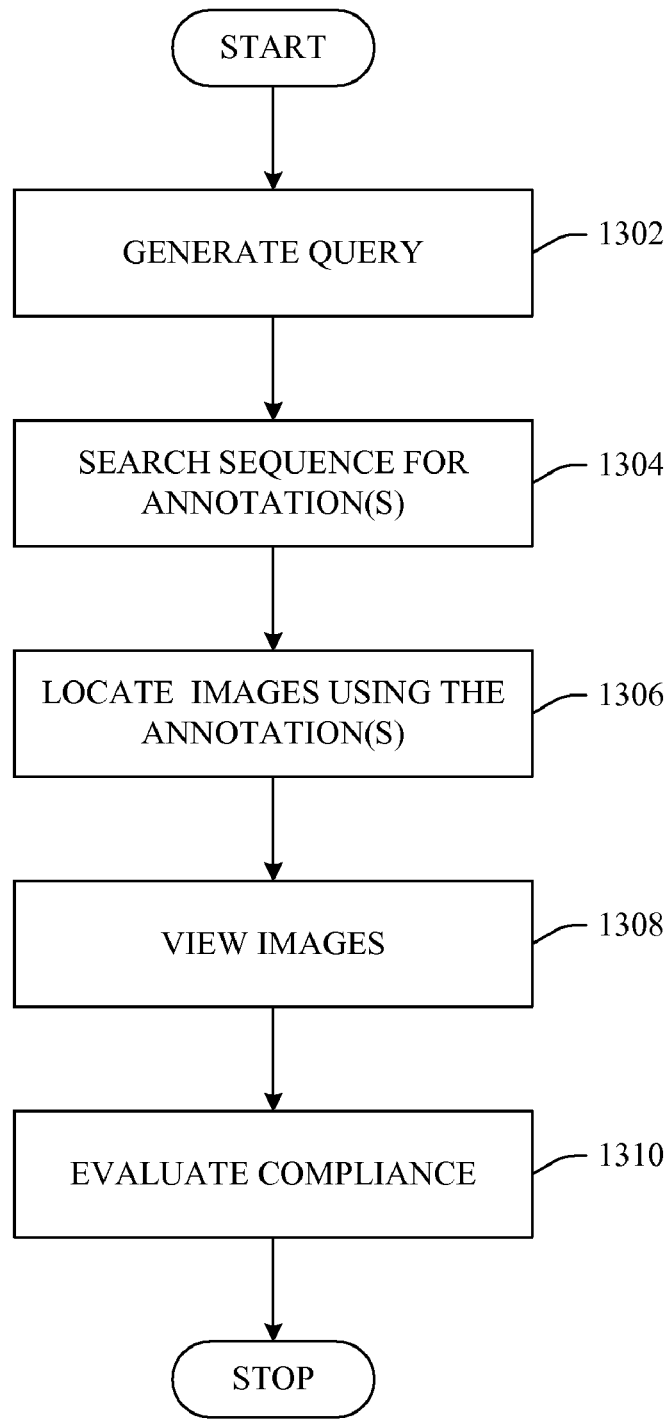
FIG. 13 illustrates an exemplary flow chart of procedures that facilitates employing annotations to enhance playback of captured images in accordance with an aspect of the innovation.

With reference now to FIG. 13, a methodology of searching for a specific event(s) and employing the events to evaluate trial compliance in accordance with the innovation is shown. Initially, at 1302, search parameters (e.g., query) can be generated. For example, search criteria can be configured to locate images that correspond to specific instances of treatment or medication use.

A search can be conducted at 1304 in order to locate desired images and/or sequences of images. In aspects, pattern and audio recognition mechanisms can be employed in order to search for and locate desired images and/or sequences that match a defined query. Similarly, these pattern and/or audio recognition systems can be employed to pre-annotate images thereafter effectuating the search and subsequent retrieval at 1306.

Once retrieved, the images can be viewed at 1308 to assist in determining compliance at 1310. Essentially, a sensor data (e.g., visual journal of sensor data) related to the use of a medication and/or treatment can be employed to determine compliance with criteria of a medical trial. Additionally, this visual journal can be searchable based upon content or other annotations (e.g., environmental data, physiological data).

Figure 14:
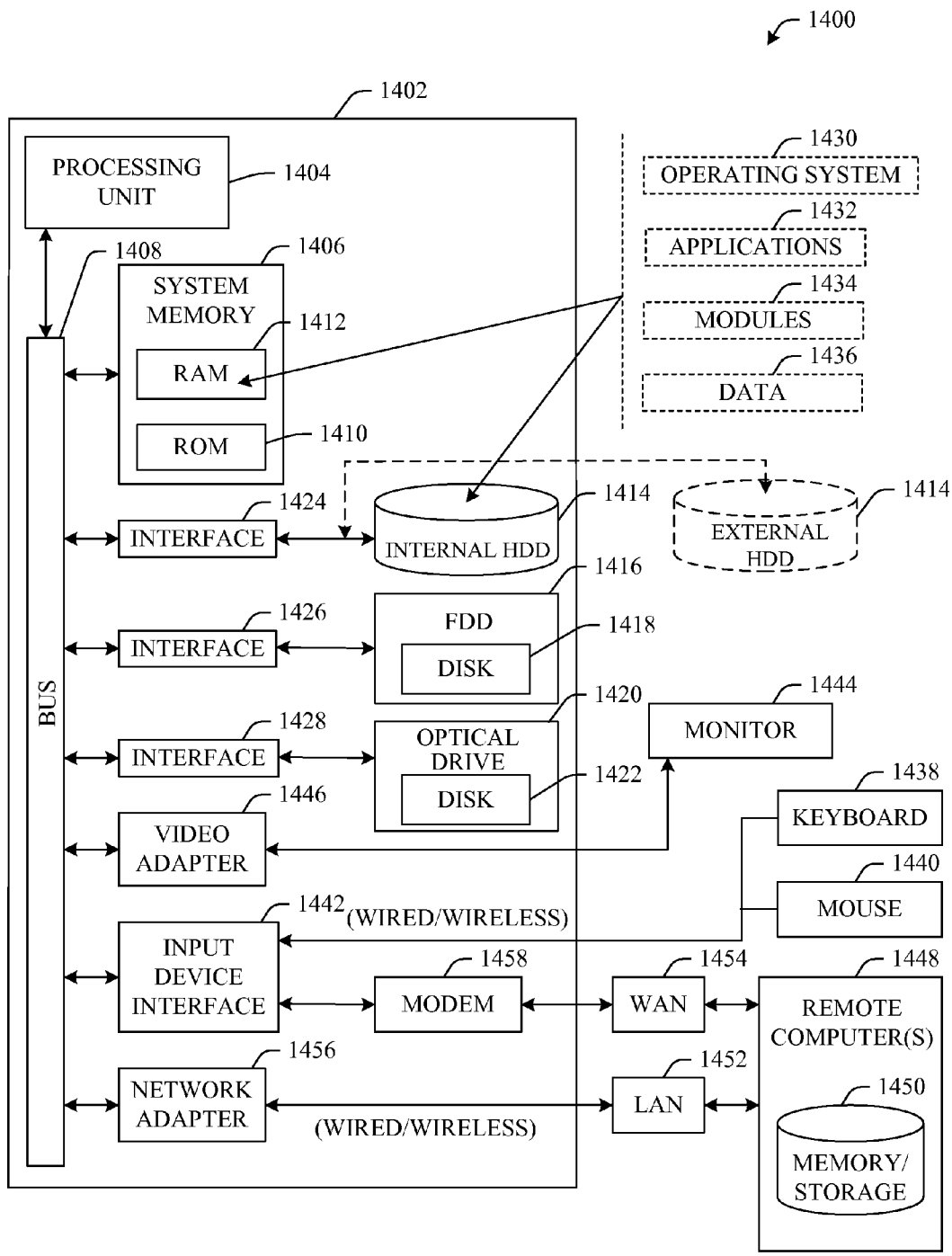
FIG. 14 illustrates a block diagram of a computer operable to execute the disclosed architecture.

Referring now to FIG. 14, there is illustrated a block diagram of a computer operable to execute the disclosed architecture of employing image capture to evaluate a clinical trial. In order to provide additional context for various aspects of the subject innovation, FIG. 14 and the following discussion are intended to provide a brief, general description of a suitable computing environment 1400 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 14, the exemplary environment 1400 for implementing various aspects of the innovation includes a computer 1402, the computer 1402 including a processing unit 1404, a system memory 1406 and a system bus 1408. The system bus 1408 couples system components including, but not limited to, the system memory 1406 to the processing unit 1404. The processing unit 1404 can be any of various commercially available processors. Dual microprocessors and other multi-processor architectures may also be employed as the processing unit 1404.

The system bus 1408 can be any of several types of bus structure that may further interconnect to a memory bus (with or without a memory controller), a peripheral bus, and a local bus using any of a variety of commercially available bus architectures. The system memory 1406 includes read-only memory (ROM) 1410 and random access memory (RAM) 1412. A basic input/output system (BIOS) is stored in a nonvolatile memory 1410 such as ROM, EPROM, EEPROM, which BIOS contains the basic routines that help to transfer information between elements within the computer 1402, such as during start-up. The RAM 1412 can also include a high-speed RAM such as static RAM for caching data.

The computer 1402 further includes an internal hard disk drive (HDD) 1414 (e.g., EIDE, SATA), which internal hard disk drive 1414 may also be configured for external use in a suitable chassis (not shown), a magnetic floppy disk drive (FDD) 1416, (e.g., to read from or write to a removable diskette 1418) and an optical disk drive 1420, (e.g., reading a CD-ROM disk 1422 or, to read from or write to other high capacity optical media such as the DVD). The hard disk drive 1414, magnetic disk drive 1416 and optical disk drive 1420 can be connected to the system bus 1408 by a hard disk drive interface 1424, a magnetic disk drive interface 1426 and an optical drive interface 1428, respectively. The interface 1424 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 1402, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 1412, including an operating system 1430, one or more application programs 1432, other program modules 1434 and program data 1436. All or portions of the operating system, applications, modules, and/or data can also be cached in the RAM 1412. It is appreciated that the innovation can be implemented with various commercially available operating systems or combinations of operating systems.

A user can enter commands and information into the computer 1402 through one or more wired/wireless input devices, e.g., a keyboard 1438 and a pointing device, such as a mouse 1440. Other input devices (not shown) may include a microphone, an IR remote control, a joystick, a game pad, a stylus pen, touch screen, or the like. These and other input devices are often connected to the processing unit 1404 through an input device interface 1442 that is coupled to the system bus 1408, but can be connected by other interfaces, such as a parallel port, an IEEE 1394 serial port, a game port, a USB port, an IR interface, etc.

A monitor 1444 or other type of display device is also connected to the system bus 1408 via an interface, such as a video adapter 1446. In addition to the monitor 1444, a computer typically includes other peripheral output devices (not shown), such as speakers, printers, etc.

The computer 1402 may operate in a networked environment using logical connections via wired and/or wireless communications to one or more remote computers, such as a remote computer(s) 1448. The remote computer(s) 1448 can be a workstation, a server computer, a router, a personal computer, portable computer, microprocessor-based entertainment appliance, a peer device or other common network node, and typically includes many or all of the elements described relative to the computer 1402, although, for purposes of brevity, only a memory/storage device 1450 is illustrated. The logical connections depicted include wired/wireless connectivity to a local area network (LAN) 1452 and/or larger networks, e.g., a wide area network (WAN) 1454. Such LAN and WAN networking environments are commonplace in offices and companies, and facilitate enterprise-wide computer networks, such as intranets, all of which may connect to a global communications network, e.g., the Internet.

When used in a LAN networking environment, the computer 1402 is connected to the local network 1452 through a wired and/or wireless communication network interface or adapter 1456. The adapter 1456 may facilitate wired or wireless communication to the LAN 1452, which may also include a wireless access point disposed thereon for communicating with the wireless adapter 1456.

When used in a WAN networking environment, the computer 1402 can include a modem 1458, or is connected to a communications server on the WAN 1454, or has other means for establishing communications over the WAN 1454, such as by way of the Internet. The modem 1458, which can be internal or external and a wired or wireless device, is connected to the system bus 1408 via the serial port interface 1442. In a networked environment, program modules depicted relative to the computer 1402, or portions thereof, can be stored in the remote memory/storage device 1450. It will be appreciated that the network connections shown are exemplary and other means of establishing a communications link between the computers can be used.

The computer 1402 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11(a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

Figure 15:
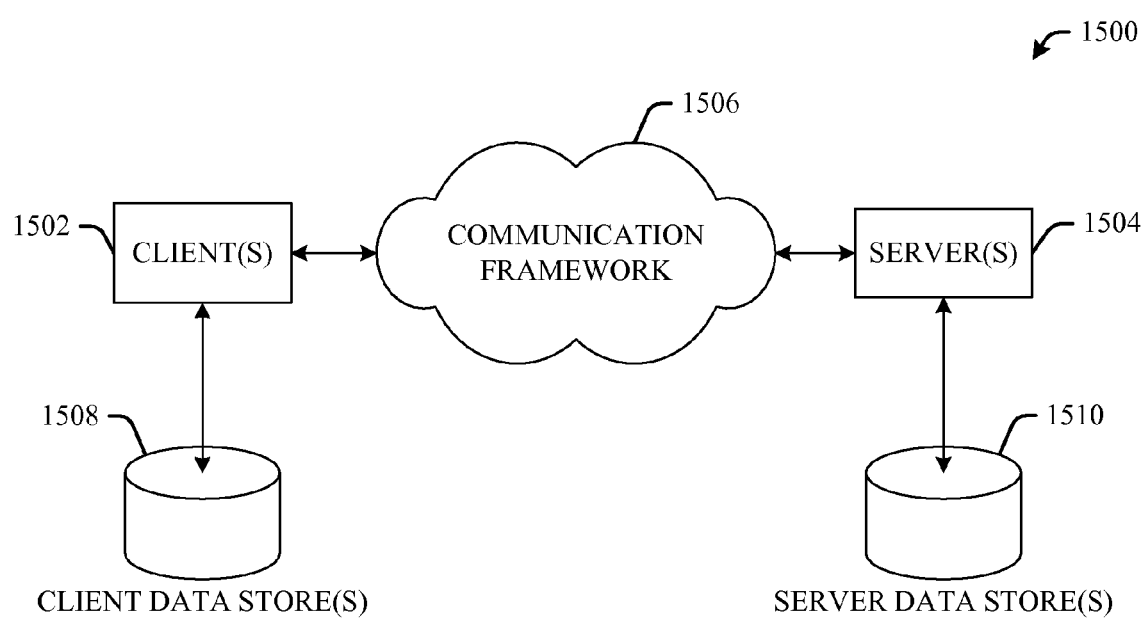
FIG. 15 illustrates a schematic block diagram of an exemplary computing environment in accordance with the subject innovation.

Referring now to FIG. 15, there is illustrated a schematic block diagram of an exemplary computing environment 1500 in accordance with the subject innovation. The system 1500 includes one or more client(s) 1502. The client(s) 1502 can be hardware and/or software (e.g., threads, processes, computing devices). The client(s) 1502 can house cookie(s) and/or associated contextual information by employing the innovation, for example.

The system 1500 also includes one or more server(s) 1504. The server(s) 1504 can also be hardware and/or software (e.g., threads, processes, computing devices). The servers 1504 can house threads to perform transformations by employing the innovation, for example. One possible communication between a client 1502 and a server 1504 can be in the form of a data packet adapted to be transmitted between two or more computer processes. The data packet may include a cookie and/or associated contextual information, for example. The system 1500 includes a communication framework 1506 (e.g., a global communication network such as the Internet) that can be employed to facilitate communications between the client(s) 1502 and the server(s) 1504.

Communications can be facilitated via a wired (including optical fiber) and/or wireless technology. The client(s) 1502 are operatively connected to one or more client data store(s) 1508 that can be employed to store information local to the client(s) 1502 (e.g., cookie(s) and/or associated contextual information). Similarly, the server(s) 1504 are operatively connected to one or more server data store(s) 1510 that can be employed to store information local to the servers 1504.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
    an event recorder component configured to automatically capture a sequence of images associated with an event, the event is a portion of a clinical trial within a given period of time;
    a sensor component configured to gather information that triggers image capture via the event recorder component;
    at least one modular add-on device configured to sense data and communicate the data to the event recorder component, the at least one modular add-on device including a wearable device having at least one of a pulse-oximeter, a stretch or range-of-motion sensor, a skin galvanic response measuring sensor, or a gait sensor, the at least one modular add-on device is configured to communicate with the event recorder component via a wireless link;
    a compliance tracker component configured to automatically monitor captured images in order to determine compliance with the clinical trial by analyzing of a subset of the images to verify dosage and timing of a medication;
    an event annotation component configured to annotate the subset of the images with contextual information to facilitate the determination of compliance; and
    a scanner component configured to capture data from textual information associated with a product, the compliance tracker configured to employ the data to assess the compliance with the clinical trial.

2. The system of claim 1, wherein the sensor component includes at least one of a physiological or an environmental sensor component.

3. The system of claim 1, further comprising:
    a sequence retrieval component configured to locate a desired sequence or image within the sequence of images based at least in part on the contextual information, the contextual information includes physiological data; and an image playback component configured to display an image or images located by the sequence retrieval component.

4. The system of claim 1, the contextual information further includes at least one of subject information, medication information, dosage information, time/date information, environmental data or physiological data.

5. The system of claim 1, the event recorder component includes a radio frequency identification (RFID) tag reader component configured to gather activity information associated with use of the product, to employ in determining the compliance with the clinical trial.

6. The system of claim 5, the event annotation component is configured to tag the subset of the images with corresponding activity information, to facilitate the compliance determination via the analyzing of the subset of the images.

7. The system of claim 1, the scanner component is configured to employ pattern recognition to recognize the textual information.

8. The system of claim 1, to annotate the subset of images with the contextual information, the event annotation component is configured to tag the subset of the images with the data captured from the textual information, to the compliance determination via the analyzing of the subset of the images.

9. The system of claim 1, further comprising an analysis component configured to automatically analyze the subset of images as a function of at least one criterion.

10. The system of claim 1, the scanner component is further configured to scan a barcode encoding information identifying at least one of a subject of the clinical trial and a dosage interval associated with the clinical trial.

11. The system of claim 1, further comprising an alert generation component configured to provide notification of a compliance deviation.

12. The system of claim 1, further comprising an interface component configured to enable playback of the subset of images.

13. The system of claim 1, further comprising a criteria management component configured to enable programmability of criteria used to determine the compliance.

14. The system of claim 1, further comprising a sequence query component configured to enable querying of captured images associated with the clinical trial.

15. A method, comprising:
automatically capturing, via an image capture device, a sequence of images of an action associated with use of a product in a clinical trial;
identifying the product at least partly by scanning textual information associated with the product, and recognizing the textual information by pattern recognition;
inferring a granularity of image capture associated with the clinical trial at least partly based on regulations imposed on the clinical trial;
monitoring environmental and physiological data to capture contextual information;
capturing a further sequence of images in accordance with the inferred granularity, based on a triggering threshold;
capturing the monitored environmental and physiological data substantially simultaneously with capturing of at least one image of the sequence of images of the action and the further sequence of images;
annotating the at least one of the images with the captured environmental and physiological data; and
determining compliance of the action as a function of a compliance criterion associated with the product, based on the sequence of images, the further sequence of images, and the contextual information.

16. The method of claim 15, further comprising:
querying an event log;
locating at least one image of the sequence of images and the further sequence of images from the event log as a function of the query; and
retrieving the at least one image of the sequence of images and the further sequence of images from the event log.

17. A computer-readable storage medium storing instructions, the instructions to, if executed by a computing device, cause the computing device to perform operations comprising:
capturing a sequence of images associated with an event;
identifying a medication by employing pattern recognition to recognize textual information associated with the medication;
annotating the images with information associated with at least one of the medication, an identity, an environmental condition, or a physiological condition;
locating a subset of the images as a function of compliance criterion; and
automatically establishing a compliance determination as a function of content of the subset of images in view of the compliance criterion.

* * * * *